United States Patent
Hong et al.

(10) Patent No.: US 12,209,258 B2
(45) Date of Patent: Jan. 28, 2025

(54) MONOOXYGENASE MUTANT AND USE THEREOF

(71) Applicant: ASYMCHEM LIFE SCIENCE (TIANJIN) CO., LTD., Tianjin (CN)

(72) Inventors: Hao Hong, Morrisville, NC (US); Gage James, Morrisville, NC (US); Jiangping Lu, Tianjin (CN); Na Zhang, Tianjin (CN); Yulei Ma, Tianjin (CN); Yibing Cheng, Tianjin (CN); Huiyan Mu, Tianjin (CN)

(73) Assignee: ASYMCHEM LIFE SCIENCE (TIANJIN) CO., LTD., Tianjin (CN)

( * ) Notice: Subject to any disclaimer, the term of this patent is extended or adjusted under 35 U.S.C. 154(b) by 426 days.

(21) Appl. No.: 17/434,436

(22) PCT Filed: Apr. 17, 2019

(86) PCT No.: PCT/CN2019/083051
§ 371 (c)(1),
(2) Date: Aug. 27, 2021

(87) PCT Pub. No.: WO2020/211013
PCT Pub. Date: Oct. 22, 2020

(65) Prior Publication Data
US 2022/0145341 A1  May 12, 2022

(51) Int. Cl.
*C12N 9/02* (2006.01)
*C12N 1/20* (2006.01)
*C12N 15/00* (2006.01)
*C12N 15/70* (2006.01)
*C12N 15/81* (2006.01)
*C12P 7/26* (2006.01)
*C12P 17/18* (2006.01)

(52) U.S. Cl.
CPC ......... *C12N 9/0073* (2013.01); *C12N 9/0004* (2013.01); *C12N 15/70* (2013.01); *C12N 15/81* (2013.01); *C12P 7/26* (2013.01); *C12P 17/188* (2013.01)

(58) Field of Classification Search
CPC ....... C12N 9/0004; C12N 9/0073; C12N 7/26
See application file for complete search history.

(56) References Cited

FOREIGN PATENT DOCUMENTS

| CN | 108048417 A | 5/2018 |
|---|---|---|
| CN | 108300707 A | 7/2018 |
| CN | 109402074 A | 3/2019 |

OTHER PUBLICATIONS

Q9A7C5_CAUVC. UniProtKB/TrEMBL. Mar. 28, 2018.*
Sanavia. Computational and Structural Biotechnology Journal, vol. 18, 2020, pp. 1968-1979.*
Fransceus. J Ind Microbiol Biotechnol. May 2017;44(4-5):687-695.*
Studer (Residue mutations and their impact on protein structure and function: detecting beneficial and pathogenic changes. Biochem. J. (2013) 449, 581-594.*
GenBank Accession No. 6ERA_A, dated Oct. 5, 2018; https://www.ncbi.nlm.nih.gov/protein/6ERA_A/.
GenBank Accession No. WP_005562951, dated May 13, 2017, https://www.ncbi.nlm.nih.gov/protein/wp_005562951.
GenBank Accession No. WP_095867568, dated Sep. 26, 2017, https://www.ncbi.nlm.nih.gov/protein/wp_095867568.
Messiha, H.L., et al., "Biocatalytic Routes to Lactone Monomers for Polymer Production", Biochemistry, Mar. 13, 2018, 57: 1997-2008.
International Search Report (ISR) for PCT/CN2019/083051 mailed Jan. 17, 2020.
Ahmad Mirza et al: "Crystal Structures of Cyclohexanone Monooxygenase Reveal Complex Domain Movements and a Sliding Cofactor", Journal of the American Chemical Society, 2009, 131:8848-8854.
Polyak Iakov et al: "Quantum Mechanical/Molecular Mechanical Study on the Enantioselectivity of the Enzymatic Baeyer-Villiger Reaction of 4-Hydroxycyclohexanone", Journal of Physical Chemistry Part B, 2013, 117:4993-5001.
Yachnin Brahm J. et al: "Lactone-Bound Structures of Cyclohexanone Monooxygenase Provide Insight into the Stereochemistry of Catalysis", ACS Chemical Biology, 2014, 9:2843-2851.
Yachnin Brahm J. et al: "The Substrate-Bound Crystal Structure of a Baeyer-Villiger Monooxygenase Exhibits a Criegee-like Conformation", Journal of the American Chemical Society, 2012, 134:7788-7795.
Messiha et al., "Biocatalytic Routes to Lactone Monomers for Polymer Production", Biochemistry, 2018, 57, 1997-2008.

* cited by examiner

*Primary Examiner* — Yong D Pak
(74) *Attorney, Agent, or Firm* — Riverside Law LLP

(57) ABSTRACT

Disclosed are a monooxygenase mutant and use thereof. An amino acid sequence of a monooxygenase mutant is an amino acid sequence obtained by mutating an amino acid sequence as shown in SEQ ID NO: 1. Mutation includes at least one of the following mutation sites: site 49, site 60, site 61, site 144, site 145, site 146, site 147, site 167, site 169, site 189, site 246, site 247, site 280, site 284, site 285, site 286, site 287, site 328, site 330, site 332, site 382, site 427, site 428, site 429, site 430, site 431, site 432, site 433, site 434, site 435, site 436, site 438, site 441, site 493, site 494, site 508, site 509, site 510, site 511, site 512, and site 513 sites and the like.

18 Claims, No Drawings
Specification includes a Sequence Listing.

SEQUENCE LISTING

<160> NUMBER OF SEQ ID NOS: 1

<210> SEQ ID NO 1
<211> LENGTH: 541
<212> TYPE: PRT
<213> ORGANISM: Rhodococcus sp.

<400> SEQUENCE: 1

Met Thr Ala Gln Ile Ser Pro Thr Val Val Asp Ala Val Val Ile Gly
1               5                   10                  15

Ala Gly Phe Gly Gly Ile Tyr Ala Val His Lys Leu His Asn Glu Gln
                20                  25                  30

Gly Leu Thr Val Val Gly Phe Asp Lys Ala Asp Gly Pro Gly Gly Thr
            35                  40                  45

Trp Tyr Trp Asn Arg Tyr Pro Gly Ala Leu Ser Asp Thr Glu Ser His
    50                  55                  60

Leu Tyr Arg Phe Ser Phe Asp Arg Asp Leu Leu Gln Asp Gly Thr Trp
65                  70                  75                  80

```
Lys Thr Thr Tyr Ile Thr Gln Pro Glu Ile Leu Glu Tyr Leu Glu Ser
                85                  90                  95

Val Val Asp Arg Phe Asp Leu Arg Arg His Phe Arg Phe Gly Thr Glu
            100                 105                 110

Val Thr Ser Ala Ile Tyr Leu Glu Asp Glu Asn Leu Trp Glu Val Ser
            115                 120                 125

Thr Asp Lys Gly Glu Val Tyr Arg Ala Lys Tyr Val Asn Ala Val
    130                 135                 140

Gly Leu Leu Ser Ala Ile Asn Phe Pro Asp Leu Pro Gly Leu Asp Thr
145                 150                 155                 160

Phe Glu Gly Glu Thr Ile His Thr Ala Ala Trp Pro Gly Lys Asn
                165                 170                 175

Leu Ala Gly Lys Arg Val Gly Val Ile Gly Thr Gly Ser Thr Gly Gln
            180                 185                 190

Gln Val Ile Thr Ala Leu Ala Pro Glu Val Glu His Leu Thr Val Phe
        195                 200                 205

Val Arg Thr Pro Gln Tyr Ser Val Pro Val Gly Asn Arg Pro Val Thr
    210                 215                 220

Lys Glu Gln Ile Asp Ala Ile Lys Ala Asp Tyr Asp Gly Ile Trp Asp
225                 230                 235                 240

Ser Val Lys Lys Ser Ala Val Ala Phe Gly Phe Glu Glu Ser Thr Leu
                245                 250                 255

Pro Ala Met Ser Val Ser Glu Glu Arg Asn Arg Ile Phe Gln Glu
                260                 265                 270

Ala Trp Asp His Gly Gly Phe Arg Phe Met Phe Gly Thr Phe Gly
                275                 280                 285

Asp Ile Ala Thr Asp Glu Ala Ala Asn Glu Ala Ala Ala Ser Phe Ile
    290                 295                 300

Arg Ser Lys Ile Ala Glu Ile Ile Glu Asp Pro Glu Thr Ala Arg Lys
305                 310                 315                 320

Leu Met Pro Thr Gly Leu Tyr Ala Lys Arg Pro Leu Cys Asp Asn Gly
                325                 330                 335

Tyr Tyr Glu Val Tyr Asn Arg Pro Asn Val Gly Ala Val Ala Ile Lys
                340                 345                 350

Glu Asn Pro Ile Arg Glu Val Thr Ala Lys Gly Val Val Thr Glu Asp
            355                 360                 365

Gly Val Leu His Glu Leu Asp Val Leu Val Phe Ala Thr Gly Phe Asp
    370                 375                 380

Ala Val Asp Gly Asn Tyr Arg Arg Ile Glu Ile Arg Gly Arg Asn Gly
385                 390                 395                 400

Leu His Ile Asn Asp His Trp Asp Gly Gln Pro Thr Ser Tyr Leu Gly
                405                 410                 415

Val Thr Thr Ala Asn Phe Pro Asn Trp Phe Met Val Leu Gly Pro Asn
            420                 425                 430

Gly Pro Phe Thr Asn Leu Pro Pro Ser Ile Glu Thr Gln Val Glu Trp
        435                 440                 445

Ile Ser Asp Thr Val Ala Tyr Ala Glu Arg Asn Glu Ile Arg Ala Ile
    450                 455                 460

Glu Pro Thr Pro Glu Ala Glu Glu Trp Thr Gln Thr Cys Thr Asp
465                 470                 475                 480

Ile Ala Asn Ala Thr Leu Phe Thr Arg Gly Asp Ser Trp Ile Phe Gly
                485                 490                 495
```

```
Ala Asn Val Pro Gly Lys Lys Pro Ser Val Leu Phe Tyr Leu Gly Gly
            500             505                 510

Leu Gly Asn Tyr Arg Asn Val Leu Ala Gly Val Val Ala Asp Ser Tyr
        515             520                 525

Arg Gly Phe Glu Leu Lys Ser Ala Val Pro Val Thr Ala
    530             535             540
```

MONOOXYGENASE MUTANT AND USE THEREOF

CROSS-REFERENCE TO RELATED APPLICATIONS

The present application is a 35 U.S.C. § 371 national phase application of International Application PCT/CN2019/083051, filed on Apr. 17, 2019, the disclosure of which is hereby incorporated by reference herein in its entirety.

SEQUENCE LISTING

The present application contains a Sequence Listing, which has been submitted electronically in ASCII format and is hereby incorporated by reference in its entirety. Said ASCII copy is named_206418_0003_00US_SequenceListing_ST25.txt and is 5.0 kilobytes in size, and contains SEQ ID NO:1, which is identical to the sequence listing filed in the corresponding international application No. PCT/CN2019/083051, filed on Apr. 17, 2019.

TECHNICAL FIELD

The present disclosure relates to the biotechnical field, in particular to a monooxygenase mutant and use thereof.

BACKGROUND

Most conventional chemical oxidizing agents are toxic and/or explosive and are very low in stereoselectivity. In order to be environmentally friendly and to synthesize high optical purity drugs and agricultural chemicals, people are developing novel oxidizing agents continuously. Cyclohexanone monooxygenase (CHMO) which is a reduced coenzyme I (NADPH) dependent oxidase can catalyze oxidizing reactions of ketones, aldehydes and some sulfides and selenides. Monooxygenase which is widely applied in organic synthesis has better selectivity, controllability and economical efficiency. With regard to synthesis of chiral drugs, products are quite different in function and toxicity usually as configurations are different. Therefore, it is quite important to obtain high optical purity chiral compounds in pharmaceutical research and development. In recent decades, monooxygenase has been used as a biological catalyst all the time in reactions for catalyzing stereoselectivity to further synthesize a series of valuable chiral compounds [Protein Engineering of Stereoselective Baeyer-Villiger Monooxygenases]. [J]. Chemistry-A European Journal, 2012, 18 (33).

As one of penem antibiotics, sulopenem researched and developed by Pfizer of America is a penem antibiotic for injection and has the characteristics of being wide in antibacterial spectrum, strong in antibacterial activity and difficult to be hydrolyzed by beta-lactamase [Antibacterial activity of sulopenem, a new parenteral penem antibiotic]. [J]. *Japanese Journal of Antibiotics*, 1996, 49 (4):338. Sulopenem plays a more and more important role in the antibiotic market in the world.

Because of advantages of high selectivity and environmental-friendliness and the like, sulopenem synthesized asymmetrically by means of a biological enzyme method is brought into focus increasingly. (R)-3-hydroxy-tetrahydrothiophene is a key intermediate for producing various drugs such as antibiotic sulopenem. In a method of enzymatic synthesis of a side chain of sulopenem (see diagram below), we has obtained a ketoreductase mutant with greatly improved selectivity and activity through protein modification, and 3-keto-tetrahydrothiophene in the first step can be catalytically converted into (R)-3-hydroxy-tetrahydrothiophene [patent: Ketoreductase mutant and use thereof (publication number CN108048417A)]. In an enzymic catalytic reaction in the second step, the oxidizing reaction of (R)-3-hydroxy-tetrahydrothiophene can be conducted by adopting monooxygenase which replaces a chemical method to avoid a chemical exothermic reaction and generate a product (R,R)-1-oxo-hydroxy tetrahydrothiophene with high optical purity simultaneously.

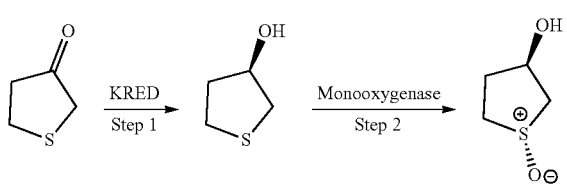 [SMILES: O=C1CCSC1 ; O[C@@H]1CCSC1 ; [O-][S@+]1CC[C@@H](O)C1]

But, for now, as wild monooxygenase has disadvantages of extremely low selectivity, poor activity and the like, there is still a big gap to perform industrial application. Generally speaking, we can modify the wild enzyme by means of protein engineering to improve the stereoselectivity and activity of the enzyme, so that the wild enzyme can be applied to industrial production.

SUMMARY

The present disclosure aims to provide a monooxygenase mutant and use thereof to solve the technical problem of poor selectivity and low enzyme activity of monooxygenase in the prior art.

In order to achieve the foregoing purpose, according to one aspect of the present disclosure, a monooxygenase mutant is provided. An amino acid sequence of the monooxygenase mutant is an amino acid sequence obtained by mutating the amino acid sequence as shown in SEQ ID NO: 1. Mutation includes at least one of the following mutation sites: site 49, site 60, site 61, site 144, site 145, site 146, site 147, site 167, site 169, site 189, site 246, site 247, site 280, site 284, site 285, site 286, site 287, site 328, site 330, site 332, site 382, site 427, site 428, site 429, site 430, site 431, site 432, site 433, site 434, site 435, site 436, site 438, site 441, site 493, site 494, site 508, site 509, site 510, site 511, site 512, and site 513 and the like, and the mutation is as follows: tryptophan at site 49 is mutated to alanine; aspartic acid at site 60 is mutated to leucine; threonine at site 61 is mutated to glutamine; valine at site 144 is mutated to glutamic acid; glycine at site 145 is mutated to phenylalanine; leucine at site 146 is mutated to phenylalanine or tyrosine; leucine at site 147 is mutated to methionine, threonine or tyrosine; histidine at site 167 is mutated to tryptophan; alanine at site 169 is mutated to lysine; serine at site 189 is mutated to methionine; alanine at site 246 is mutated to valine; valine at site 247 is mutated to threonine; phenylalanine at site 280 is mutated to tyrosine, tryptophan or valine; phenylalanine at site 284 is mutated to serine; glycine at site 285 is mutated to alanine; threonine at site 286 is mutated to alanine; phenylalanine at site 287 is mutated to aspartic acid; alanine at site 328 is mutated to asparagine; arginine at site 330 is mutated to alanine; leucine at site 332 is mutated to arginine; glycine at site 382 is mutated to alanine; methionine at site 427 is mutated to isoleucine; valine at site 428 is mutated to alanine; leucine at site 429 is mutated to tyrosine; glycine at site 430 is mutated to alanine; proline at site 431 is mutated to alanine; asparagine at site 432 is mutated to tyrosine; glycine at site 433 is mutated to tyrosine; proline at site 434 is mutated to alanine; phenylalanine at site 435 is mutated to serine, alanine, asparagine or tyrosine; threonine at site 436 is mutated to alanine, serine, glycine, glutamic acid or cysteine; leucine at site 438 is mutated to glycine, alanine, tyrosine, phenylalanine or serine; serine at site 441 is mutated to leucine and valine; tryptophan at site 493 is mutated to alanine; isoleucine at site 494 is mutated to alanine, methionine or serine, phenylalanine at site 508 is mutated to tyrosine, methionine or asparagine, and tyrosine at site 509 is mutated to methionine; leucine at site 510 is mutated to valine; glycine at site 511 is mutated to leucine; glycine at site 512 is mutated to isoleucine; leucine at site 513 is mutated to valine; or the amino acid sequence of the monooxygenase mutant has the mutation sites in the mutated amino acid sequence and has 80% or higher identity to the mutated amino acid sequence.

Further, the mutation includes at least one of the following mutation site combinations: F435A+F508Y; F435S+F508Y; L147Y+F508M; F280Y+F508M; F280Y+F508N; F435A+L510V; F435 S+L510V; F435N+L510V; T436A+L510V; L438A+L510V; T436A+L438A; F435A+T436A; F435S+T436A; F435N+T436A; L146Y+F508M; L146F+F508M; F280Y+F508Y; F280Y+F508N; F435A+T436A+F508Y; F435A+T436A+F508M; F435A+T436A+L510V; F435 S+T436A+L510V; T436A+L438A+F508Y; T436A+L438A+F508M; T436A+L438A+F508N; L147Y+F435A+F508M; L147Y+F435A+F508Y; L147Y+F435A+F508N; L147Y+F435S+F508Y; L147Y+F435N+F508Y; L147Y+F435S+F508Y; L147Y+F435N+F508Y; F508Y+F435A+L438A; F508Y+F435A+L438Y; F508Y+F435A+L438Y; F508Y+F435A+L438A+T436A; F508Y+F435A+L438A+T436S; F508M+F435A+L438A+T436A; F508M+F435A+L438A+T436S; F508Y+F435A+L438A+T436A+F280W; F508Y+F435A+L438A+T436A+F280A; F508Y+F435A+L438A+T436A+S441L; F508M+F435A+L438A+T436A+F280W; F508M+F435A+L438A+T436A+F280V; F508M+F435A+L438A+T436A+S441V; F508M+F435A+L438A+T436A+S441A; F508Y+F435N+L438A+T436S; F508Y+F435N+L438A+T436S+F280V; F508Y+F435N+L438A+T436S+S441L; F508Y+F435N+L438A+T436S+F280V+S441V; F508Y+F435N+L438A+T436S+F280V+S441V+L510V; F508M+F435N+L438A+T436S+F280V+S441V+L510V; F508M+F435A+L438A+T436S+F280V+S441V+L510V; F508M+F435S+L438A+T436S+F280V+S441V+L510V; F508Y+F435S+L438Y+T436S+F280V+S441V+L510V; F508Y+F435N+L438A+T436A+F280V+S441V+L510V; F508Y+F435N+L438A+T436A+F280V+S441A+L510V; F508Y+F435N+L438A+T436A+F280V+S441L+L510V; F508Y+F435N+L438A+T436A+F280V+S441L+L510V+L429Y+W493A+L146F+L147M+I494A; F508Y+F435N+L438A+T436A+F280V+S441L+L510V+L429Y+W493A+L146F+L147Y+I494S; F508Y+F435N+L438A+T436A+F280V+S441L+L510V+L429Y+W493A+L146F+L147T+I494M; F508Y+F435N+L438A+T436S+F280V+S441V+L510V+D60L; F508M+F435N+L438A+T436S+F280V+S441V+L510V+D60L+T61Q; F508M+F435A+L438A+T436S+F280V+S441V+L510V+D60L+G145F; F508M+F435S+L438A+T436S+F280V+S441V+L510V+D60L+A169K; F508Y+F435S+L438Y+T436S+F280V+S441V+L510V+D60L+S189M; F508Y+F435N+L438A+T436A+F280V+S441V+L510V+D60L+L332R; F508Y+F435N+L438A+T436A+F280V+S441A+L510V+D60L+A328N; F508Y+F435N+L438A+T436A+F280V+S441L+L510V+D60L+G430A; F508Y+F435N+L438A+T436A+F280V+S441L+L510V+L429Y+W493A+L146F+L147M+I494A+D60L+N432Y; F508Y+F435N+L438A+T436A+F280V+S441L+L510V+L429Y+W493A+L146F+L147Y+I494S+D60L+Y509M; F508Y+F435N+L438A+T436A+F280V+S441L+L510V+L429Y+W493A+L146F+L147T+I494M+D60L+G512I; F508Y+F435A+L438A+W49A+D60L; F508Y+F435A+L438A+V144E; F508Y+F435A+L438A+G145F; F508Y+F435A+L438A+T436A+H167W; F508Y+F435A+L438A+T436A+A169K; F508Y+F435A+L438A+T436A+S179M; F508Y+F435A+L438A+T436A+A246V; F508Y+F435A+L438A+T436A+V247T; F508Y+F435A+L438A+T436A+F284S; F508Y+F435A+L438A+T436A+G285A; F508M+F435A+L438A+T436A+T286A; F508M+F435A+L438A+T436A+R330A; F508M+F435A+L438A+T436A+L332R; F508M+F435A+L438A+T436A+A328N; F508Y+F435A+L438A+T436S+G382A; F508Y+F435A+L438A+T436S+M427I; F508Y+F435A+L438A+T436S+V428A; F508Y+F435A+L438A+T436S+G430A; F508Y+F435A+L438A+T436S+P431A; F508Y+F435A+L438A+T436S+N432Y; F508Y+F435A+L438A+T436S+G433Y; F508Y+F435A+L438A+T436S+P434A; F508Y+F435A+L438A+T436S+Y509M; F508Y+F435A+L438A+T436S+G511L; F508Y+F435A+L438A+T436S+G512I; F508Y+F435A+L438A+T436S+L513V; F508Y+F435S+L438Y+T436S+F280V+S441V+L510V+D60L; F508Y+F435N+L438A+T436A+F280V+S441V+L510V+D60L+P431A; F508Y+F435N+L438A+T436A+F280V+S441A+L510V+D60L; F508Y+F435N+L438A+T436A+F280V+S441L+L510V+D60L; F508Y+F435N+L438A+T436A+F280V+S441L+L510V+D60L+L429Y+W493A+L1 46F+L147Y+I494S; F508Y+F435N+L438A+T436A+F280V+S441L+L510V+D60L+L429Y+W493A+L1 46F+L147T+I494M; F508Y+F435A+L438Y; F508Y+F435A+L438A+T436A; F508Y+F435A+L438A+T436S; F508M+F435A+L438A+T436A; F508M+F435A+L438A+T436S; F508Y+F435A+L438A; F508Y+F435A+L438Y; F508Y+F435A+L438Y; F508Y+F435A+L438A+T436A; F508Y+F435A+L438A+T436S; F508M+F435A+L438A+T436A; F508M+F435A+L438A+T436S; F508Y+F435A+L438A+T436A+F280W+D60L; F508Y+F435A+L438A+T436A+F280A+V247T; F508Y+F435A+L438A+T436A+S441L+F285A; F508Y+F435N+L438A+T436S+R330A; F508Y+F435N+L438A+T436S+F280V+G430A; F508Y+F435N+L438A+T436S+S441L+P434A; F508M+F435N+L438A+T436S+F280V+S441V+L510V+Q60L+T286A+Y509M; F508M+F435A+L438A+T436S+F280V+S441V+L510V+Q60L+T61Q+V247T; F508M+F435 S+L438A+T436S+F280V+S441V+L510V+Q60L+F287D+R330A; F508Y+F435S+L438Y+T436S+F280V+S441V+L510V+V144E+G145F+M427I; F508Y+F435N+L438A+T436A+F280V+S441V+L510V+Q60L+L322R+N432Y; F508Y+F435N+L438A+T436A+F280V+S441A+L510V+R330A+P321A+G512I; and F508Y+F435N+L438A+T436A+F280V+S441L+L510V+T61Q+R330A+G430A.

According to another aspect of the present disclosure, a DNA molecule is provided. The DNA molecule encodes any one monooxygenase mutant above.

According to yet another aspect of the present disclosure, a recombinant plasmid is provided. The recombinant plasmid contains any one DNA molecule above.

Further, the recombinant plasmid is pET-22b(+), pET-22b(+), pET-3a(+), pET-3 d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b (+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to another aspect of the present disclosure, a host cell is provided. The host cell contains any one recombinant plasmid above.

Further, the host cell includes prokaryotic cell, yeast or eukaryocyte, and preferably, the prokaryotic cell is an *Escherichia coli* BL21 cell or an *Escherichia coli* DH5α competent cell.

According to another aspect of the present disclosure, use of any one monooxygenase mutant above in catalysis of a monooxygenation reaction of a thioether compound or a ketone compound.

Further, the thioether compound is

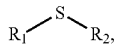

wherein $R_1$ and $R_2$ independently represent optionally substituted or unsubstituted alkyl, optionally substituted or unsubstituted aralkyl or optionally substituted or unsubstituted aryl respectively; and $R_1$ and $R_2$ can independently form optionally substituted or unsubstituted rings or can form optionally substituted or unsubstituted rings in a combined manner;

preferably, $R_1$ and $R_2$ are optionally substituted or unsubstituted alkyl, optionally substituted or unsubstituted aralkyl, or optionally substituted or unsubstituted aryl with 1-20 carbon atoms, more preferably optionally substituted or unsubstituted alkyl, optionally substituted or unsubstituted aralkyl, or optionally substituted or unsubstituted aryl with 1-10 carbon atoms;

preferably, the aryl includes phenyl, naphthyl, pyridyl, thienyl, oxadiazolyl, imidazolyl, thiazolyl, furyl, pyrryl, phenoxyl, naphthoxyl, pyridyloxy, thienyloxy, oxadiazolyloxy, imidazolyloxy, thiazolyloxy, furyloxy and pyrrolyoxy;

preferably, the alkyl includes methyl, ethyl, propyl, butyl, pentyl, hexyl, isopropyl, sec-butyl, tertiary butyl, methoxyl, ethoxyl, tert-butoxyl, methoxycarbonyl, ethoxycarbonyl, tert-butoxycarbonyl, vinyl, allyl, cyclopentyl and cycloheptyl;

preferably, the aralkyl is benzyl;

and preferably, being substituted means being substituted by a halogen atom, a nitrogen atom, a sulfur atom, hydroxyl, nitryl, cyano, methoxyl, ethoxyl, carboxyl, carboxymethyl, carboxymethyl or methylenedioxyl.

Further, the ketone compound is

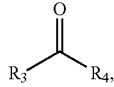

wherein $R_3$ and $R_4$ independently represent optionally substituted or unsubstituted alkyl, optionally substituted or unsubstituted aralkyl or optionally substituted or unsubstituted aryl respectively; and $R_3$ and $R_4$ can independently form optionally substituted or unsubstituted rings or can form optionally substituted or unsubstituted rings in a combined manner;

preferably, $R_3$ and $R_4$ are optionally substituted or unsubstituted alkyl, optionally substituted or unsubstituted aralkyl, or optionally substituted or unsubstituted aryl with 1-20 carbon atoms, more preferably optionally substituted or unsubstituted alkyl, optionally substituted or unsubstituted aralkyl, or optionally substituted or unsubstituted aryl with 1-10 carbon atoms;

preferably, the aryl includes phenyl, naphthyl, pyridyl, thienyl, oxadiazolyl, imidazolyl, thiazolyl, furyl, pyrryl, phenoxyl, naphthoxyl, pyridyloxy, thienyloxy, oxadiazolyloxy, imidazolyloxy, thiazolyloxy, furyloxy and pyrrolyoxy;

preferably, the alkyl includes methyl, ethyl, propyl, butyl, pentyl, hexyl, isopropyl, sec-butyl, tertiary butyl, methoxyl, ethoxyl, tert-butoxyl, methoxycarbonyl, ethoxycarbonyl, tert-butoxycarbonyl, vinyl, allyl, cyclopentyl and cycloheptyl;

preferably, the aralkyl is benzyl;

and preferably, being substituted means being substituted by a halogen atom, a nitrogen atom, a sulfur atom, hydroxyl, nitryl, cyano, methoxyl, ethoxyl, carboxyl, carboxymethyl, carboxymethyl or methylenedioxyl.

Further, the application is synthesis of a side chain of sulopenem.

Further, the monooxygenase is a solution, lyophilized powder, an immobilized enzyme or an immobilized cell of the above any one monooxygenase mutant.

Further, a reaction system of the monooxygenation reaction further includes a cofactor. The cofactor is NAD+/NADH and/or NADP+/NADPH. A circulatory system of the cofactor includes glucose and glucose dehydrogenase, formate and formate dehydrogenase, glucose-6-phosphoric acid and glucose-6-phosphate dehydrogenase or secondary alcohol or secondary alcohol dehydrogenase.

Further, a temperature of the monooxygenation reaction ranges from 10 to 37° C., preferably 15 to 35° C.

Further, a time of the monooxygenation reaction is 3-48 hours, more preferably 6-16 hours.

Further, the monooxygenation reaction is conducted under a condition of pH 5.0-10.0, preferably pH 6.0-9.0.

Based the monooxygenase as shown in the SEQ ID NO: 1, the monooxygenase mutant mutates by way of site-directed mutation to change the amino acid sequence so as to change structure and function of a protein and obtains the monooxygenase with the mutation sites by way of directed screening. The monooxygenase mutant has the advantage of greatly improved stereoselectivity, and the enzyme activity is also improved correspondingly.

DETAILED DESCRIPTION

It should be noted that in the absence of conflict, the embodiments of the present disclosure and features in the embodiments can be combined with one another. Detail description on the present disclosure will be made below in combination with the embodiments.

The monooxygenase originated from *Rhodococcus* sp. can catalyze the thioether compound and the ketone compound to react. However, the monooxygenase is low in activity and poor in stereoselectivity, especially for the oxidation of (R)-3-hydroxy-tetrahydrothiophene, the product obtained is S-type, and the configuration is opposite to the target product. The present disclosure tries hard to improve the stereoselectivity of the monooxygenase and the activity of the monooxygenase by means of protein engineering, so as to obtain the mutant with an improved enzymatic catalytic characteristic. In a production and preparation process of the chiral compound, the dosage of the enzyme is reduced, and a product with high optical purity is obtained.

The inventor of the present disclosure improves the activity and stereoselectivity of the monooxygenase as shown in the SEQ ID NO: 1 by means of directed evolution and reduces the dosage of the enzyme. First, the mutation sites are introduced into the monooxygenase as shown in the SEQ ID NO: 1 by way of whole-plasmid PCR, detect the activity and stereoselectivity of the mutants and the mutants with improved activity or stereoselectivity are selected.

SEQ ID NO: 1 is shown in as follows: MTAQISPTVV-DAVVIGAGFGGIYAVHKLHNEQGLTVVGFDK ADGPGGTWYWNRYPGALSDTESH-LYRFSFDRDLLQDGTWKTTYITQPEILEY LESVVDRFDLRRHFRFGTEVTSAIYLEDENLW-EVSTDKGEVYRAKYVVNAV GLLSAINFPDLPGLDT-FEGETIHTAAWPEGKNLAGKRVGVIGTGSTGQQVITA LAPEVEHLTVFVRTPQYSVPVGNRPVTKEQIDAI-KADYDGIWDSVKKSAVAF GFEESTLPAMSV-SEEERNRIFQEAWDHGGGFRFMFGTFGDIATDEAA-NEAAA SFIRSKIAEIIEDPETARKLMPTGLYAKR-PLCDNGYYEVYNRPNVEAVAIKENP IREVTAKGVVT-EDGVLHELDVLVFATGFDAVDGNYRRIEIRGRNGL-HINDHW DGQPTSYLGVTTANFPNWFMVLGPNGPFTNLPPSI-ETQVEWISDTVAYAERN EIRAIEPTPEAEEEWTQTCT-DIANATLFTRGDSWIFGANVPGKKP SVLFYLGGL GNYRNVLAGVVADSYRGFELKSAVPVTA. By taking the SEQ ID NO: 1 as a template, 60 pairs of site-directed mutation primers are designed (the mutation sites are the site 49, site 60, site 61, site 144, site 145, site 146, site 147, site 167, site 169, site 189, site 246, site 247, site 280, site 284, site 285, site 286, site 287, site 328, site 330, site 332, site 382, site 427, site 428, site 429, site 430, site 431, site 432, site 433, site 434, site 435, site 436, site 438, site 441, site 493, site 494, site 508, site 509, site 510, site 511, site 512, and site 513). By means of site-directed mutation and taking pET-22b (+) as an expression vector, a mutation plasmid with a target gene is obtained.

Herein, the site-directed mutation is that: through methods of a polymerase chain reaction (PCR) and the like, a required change (generally a change of representing a beneficial direction) is introduced in a target DNA fragment (may be a genome, or may be a plasmid), including addition, deletion, point mutation and the like of a basic group. The site-directed mutation is capable of rapidly and efficiently improving characters and representation of a target protein expressed by a DNA, and is a very useful tool in gene research work.

The method for introducing the site-directed mutation by using the whole-plasmid PCR is simple and effective, and is a method used more at present. A principle thereof is that after a pair of primers (forward and reverse) containing mutation sites are annealed with a template plasmid, "cyclic extension" is performed by using a polymerase, and the so-called cyclic extension is that the polymerase extends the primer according to the template, is returned to a 5'-terminal of the primer and terminated after one circle, and subjected to a cycle of repeatedly heated and annealed extension, this reaction is different from rolling circle amplification, and does not form multiple tandem copies. Extension products of the forward and reverse primers are paired to form an open-circle plasmid with an incision after annealed. A Dpn I enzyme-digested extension product, because the original template plasmid is derived from conventional *Escherichia coli*, is modified by dam methylation, and is sensitive to Dpn I so as to be shredded, but a plasmid with a mutant sequence synthesized in vitro is not cut because it is not methylated, so it may be successfully transformed in subsequent transformation, and a clone of a mutant plasmid may be obtained.

the mutant plasmid was transformed into *E. coli* cells, plated in LB culture dishes containing 100 μg/ml penbritin, and incubated overnight at 37° C. A monoclone growing on the solid medium is activated. After the site-directed mutants were identified by sequencing, the expression of monooxygenase was incubated at 25° C., and induced by 0.2 mM IPTG overnight. Then the crude enzyme was obtained by ultrasonication of cells, which was used to detect the reaction characteristics.

On a basis of the mutant with the improved catalytic property obtained by single site-directed mutation, beneficial sites can be combined to obtain a mutant with more excellent characters. A construction method of double site mutation is as same as a construction method of single site mutation in combined mutation and the double site mutation and the single site mutation are constructed by adopting an whole-plasmid PCR method. Multisite mutation with mutations on two or more sites is conducted by gene splicing by overlap extension PCR amplification to obtain a mutant gene containing multisite mutations. The mutant gene double-digested by a restriction enzyme at two ends is connected to an expression vector, is transformed into the *Escherichia coli* cell, plated in the LB culture dishes containing 100 μg/mL penbritin and is cultured overnight at 37° C. to obtain a combined mutant subjected to sequencing authentication.

Gene splicing by overlap extension PCR, SOEPCR for short, is to form overlapped chains by a PCR product by adopting the primers with complementary tail ends, such that amplified fragments from different sources are overlapped and spliced by extending the overlapped chains in a subsequent amplification reaction. The technology which can perform genetic recombination in vitro by means of the PCR technology is usually used in construction of multisite mutation.

By performing abutting simulation analysis on three-dimensional structures of monooxygenase and a substrate by using a computer, it is found near an enzyme catalytic center that distances from some amino acids to the substrate are 5A, which may be closely connected with stereoselectivity and activity of the enzyme to the substrate. Based on multisite combined mutation, iterative saturated mutation on these amino acid sites which may be affected is performed to obtain the mutant with greatly improved activity and stereoselectivity.

Saturated mutation is a method of obtaining a mutant, amino acids at target sites of which are substituted by other 19 amino acids, within a short time by modifying an encoding gene of a target protein. The method is not only a powerful tool for directional transformation of the protein, but also is an important means for researching a relationship between structure and function of the protein. Compared with single site mutation, saturated mutation often can obtain a more ideal evolution body. It is just unique for the saturated mutation method to solve the problems which cannot be solved by the site-directed mutation method.

According to a typical embodiment of the present disclosure, a monooxygenase mutant is provided. An amino acid sequence of the monooxygenase mutant is an amino acid sequence obtained by mutating an amino acid sequence as shown in SEQ ID NO: 1. Mutation includes at least one of the following mutation sites: site 49, site 60, site 61, site 144, site 145, site 146, site 147, site 167, site 169, site 189, site 246, site 247, site 280, site 284, site 285, site 286, site 287, site 328, site 330, site 332, site 382, site 427, site 428, site 429, site 430, site 431, site 432, site 433, site 434, site 435, site 436, site 438, site 441, site 493, site 494, site 508, site 509, site 510, site 511, site 512, and site 513 and the like, and the mutation is as follows: tryptophan at site 49 is mutated to alanine; aspartic acid at site 60 is mutated to leucine; threonine at site 61 is mutated to glutamine; valine at site 144 is mutated to glutamic acid; glycine at site 145 is mutated to phenylalanine; leucine at site 146 is mutated to phenylalanine or tyrosine; leucine at site 147 is mutated to methionine, threonine or tyrosine; histidine at site 167 is mutated to tryptophan; alanine at site 169 is mutated to lysine; serine at site 189 is mutated to methionine; alanine at site 246 is mutated to valine; valine at site 247 is mutated to threonine; phenylalanine at site 280 is mutated to tyrosine, tryptophan or valine; phenylalanine at site 284 is mutated to serine; glycine at site 285 is mutated to alanine; threonine at site 286 is mutated to alanine; phenylalanine at site 287 is mutated to aspartic acid; alanine at site 328 is mutated to asparagine; arginine at site 330 is mutated to alanine; leucine at site 332 is mutated to arginine; glycine at site 382 is mutated to alanine; methionine at site 427 is mutated to isoleucine; valine at site 428 is mutated to alanine; leucine at site 429 is mutated to tyrosine; glycine at site 430 is mutated to alanine; proline at site 431 is mutated to alanine; asparagine at site 432 is mutated to tyrosine; glycine at site 433 is mutated to tyrosine; proline at site 434 is mutated to alanine; phenylalanine at site 435 is mutated to serine, alanine, asparagine or tyrosine; threonine at site 436 is mutated to alanine, serine, glycine, glutamic acid or cysteine; leucine at site 438 is mutated to glycine, alanine, tyrosine, phenylalanine or serine; serine at site 441 is mutated to leucine and valine; tryptophan at site 493 is mutated to alanine; isoleucine at site 494 is mutated to alanine, methionine or serine, phenylalanine at site 508 is mutated to tyrosine, methionine or asparagine, and tyrosine at site 509 is mutated to methionine; leucine at site 510 is mutated to valine; glycine at site 511 is mutated to leucine; glycine at site 512 is mutated to isoleucine; leucine at site 513 is mutated to valine; or the amino acid sequence of the monooxygenase mutant has the mutation sites in the mutated amino acid sequence and has 80% or higher identity to the mutated amino acid sequence.

The mutant with improved ee value and activity is obtained by verifying activity via the reaction. Specifically speaking, preferably, the mutation at least includes one of the following mutation site combinations: F435A+F508Y; F435S+F508Y; L147Y+F508M; F280Y+F508M; F280Y+ F508N; F435A+L510V; F435S+L510V; F435N+L510V; T436A+L510V; L438A+L510V; T436A+L438A; F435A+ T436A; F435S+T436A; F435N+T436A; L146Y+F508M; L146F+F508M; F280Y+F508Y; F280Y+F508N; F435A+ T436A+F508Y; F435A+T436A+F508M; F435A+T436A+ L510V; F435S+T436A+L510V; T436A+L438A+F508Y; T436A+L438A+F508M; T436A+L438A+F508N; L147Y+ F435A+F508M; L147Y+F435A+F508Y; L147Y+F435A+ F508N; L147Y+F435S+F508Y; L147Y+F435N+F508Y; L147Y+F435S+F508Y; L147Y+F435N+F508Y; F508Y+ F435A+L438A; F508Y+F435A+L438Y; F508Y+F435A+ L438Y; F508Y+F435A+L438A+T436A; F508Y+F435A+ L438A+T436S; F508Y+F435A+L438A+T436A; F508M+ F435A+L438A+T436S; F508Y+F435A+L438A+T436A+ F280W; F508Y+F435A+L438A+T436A+F280A; F508Y+ F435A+L438A+T436A+S441L; F508M+F435A+L438A+ T436A+F280W; F508M+F435A+L438A+T436A+F280V; F508M+F435A+L438A+T436A+S441V; F508M+F435A+ L438A+T436A+S441A; F508Y+F435N+L438A+T436S; F508Y+F435N+L438A+T436S+F280V; F508Y+F435N+ L438A+T436S+S441L; F508Y+F435N+L438A+T436S+ F280V+S441V; F508Y+F435N+L438A+T436S+F280V+ S441V+L510V; F508M+F435N+L438A+T436S+F280V+ S441V+L510V; F508M+F435A+L438A+T436S+F280V+ S441V+L510V; F508M+F435S+L438A+T436S+F280V+ S441V+L510V; F508Y+F435S+L438Y+T436S+F280V+ S441V+L510V; F508Y+F435N+L438A+T436A+F280V+ S441V+L510V; F508Y+F435N+L438A+T436A+F280V+ S441A+L510V; F508Y+F435N+L438A+T436A+F280V+ S441L+L510V; F508Y+F435N+L438A+T436A+F280V+ S441L+L510V+L429Y+W493A+L146F+L147M+I494A; F508Y+F435N+L438A+T436A+F280V+S441L+L510V+ L429Y+W493A+L146F+L147Y+I494S; F508Y+F435N+ L438A+T436A+F280V+S441L+L510V+L429Y+W493A+ L146F+L147T+I494M; F508Y+F435N+L438A+T436S+ F280V+S441V+L510V+D60L; F508M+F435N+L438A+ T436S+F280V+S441V+L510V+D60L+T61Q; F508M+ F435A+L438A+T436S+F280V+S441V+L510V+D60L+ G145F; F508M+F435S+L438A+T436S+F280V+S441V+ L510V+D60L+A169K; F508Y+F435S+L438Y+T436S+ F280V+S441V+L510V+D60L+S189M; F508Y+F435N+ L438A+T436A+F280V+S441V+L510V+D60L+L332R; F508Y+F435N+L438A+T436A+F280V+S441A+L510V+ D60L+A328N; F508Y+F435N+L438A+T436A+F280V+ S441L+L510V+D60L+G430A; F508Y+F435N+L438A+ T436A+F280V+S441L+L510V+L429Y+W493A+L146F+ L147M+I494A+D60L+N432Y; F508Y+F435N+L438A+ T436A+F280V+S441L+L510V+L429Y+W493A+L146F+ L147Y+I494S+D60L+Y509M; F508Y+F435N+L438A+ T436A+F280V+S441L+L510V+L429Y+W493A+L146F+ L147T+I494M+D60L+G512I; F508Y+F435A+L438A+ W49A+D60L; F508Y+F435A+L438A+V144E; F508Y+ F435A+L438A+G145F; F508Y+F435A+L438A+T436A+ H167W; F508Y+F435A+L438A+T436A+A169K; F508Y+ F435A+L438A+T436A+S179M; F508Y+F435A+L438A+ T436A+A246V; F508Y+F435A+L438A+T436A+V247T; F508Y+F435A+L438A+T436A+F284S; F508Y+F435A+ L438A+T436A+G285A; F508M+F435A+L438A+T436A+ T286A; F508M+F435A+L438A+T436A+R330A; F508M+ F435A+L438A+T436A+L332R; F508M+F435A+L438A+ T436A+A328N; F508Y+F435A+L438A+T436S+G382A; F508Y+F435A+L438A+T436S+M427I; F508Y+F435A+ L438A+T436S+V428A; F508Y+F435A+L438A+T436S+ G430A; F508Y+F435A+L438A+T436S+P431A; F508Y+ F435A+L438A+T436S+N432Y; F508Y+F435A+L438A+ T436S+G433Y; F508Y+F435A+L438A+T436S+P434A; F508Y+F435A+L438A+T436S+Y509M; F508Y+F435A+ L438A+T436S+G511L; F508Y+F435A+L438A+T436S+ G512I; F508Y+F435A+L438A+T436S+L513V; F508Y+ F435S+L438Y+T436S+F280V+S441V+L510V+D60L; F508Y+F435N+L438A+T436A+F280V+S441V+L510V+ D60L+P431A; F508Y+F435N+L438A+T436A+F280V+ S441A+L510V+D60L; F508Y+F435N+L438A+T436A+ F280V+S441L+L510V+D60L; F508Y+F435N+L438A+ T436A+F280V+S441L+L510V+D60L+L429Y+W493A+ L1 46F+L147Y+I494S; F508Y+F435N+L438A+T436A+ F280V+S441L+L510V+D60L+L429Y+W493A+L1 46F+ L147T+I494M; F508Y+F435A+L438Y; F508Y+F435A+ L438A+T436A; F508Y+F435A+L438A+T436S; F508M+ F435A+L438A+T436A; F508M+F435A+L438A+T436S; F508Y+F435A+L438A; F508Y+F435A+L438Y; F508Y+ F435A+L438Y; F508Y+F435A+L438A+T436A; F508Y+ F435A+L438A+T436S; F508M+F435A+L438A+T436A;

F508M+F435A+L438A+T436S; F508Y+F435A+L438A+ T436A+F280W+D60L; F508Y+F435A+L438A+T436A+ F280A+V247T; F508Y+F435A+L438A+T436A+S441L+ F285A; F508Y+F435N+L438A+T436S+R330A; F508Y+ F435N+L438A+T436S+F280V+G430A; F508Y+F435N+ L438A+T436S+S441L+P434A; F508M+F435N+L438A+ T436S+F280V+S441V+L510V+Q60L+T286A+Y509M; F508M+F435A+L438A+T436S+F280V+S441V+L510V+ Q60L+T61Q+V247T; F508M+F435 S+L438A+T436S+ F280V+S441V+L510V+Q60L+F287D+R330A; F508Y+ F435S+L438Y+T436S+F280V+S441V+L510V+V144E+ G145F+M427I; F508Y+F435N+L438A+T436A+F280V+ S441V+L510V+Q60L+L322R+N432Y; F508Y+F435N+ L438A+T436A+F280V+S441A+L510V+R330A+P321A+ G512I; and F508Y+F435N+L438A+T436A+F280V+ S441L+L510V+T61Q+R330A+G430A. For the convenience of description, phenylalanine on the 435th site is mutated into alanine and phenylalanine on the 508th site is mutated into tyrosine, which is described as F435A+ F508Y; it is similar with other specifications.

Based the monooxygenase as shown in the SEQ ID NO: 1, the monooxygenase mutant mutates by way of site-directed mutation to change the amino acid sequence so as to change structure and function of a protein and obtains the monooxygenase with the mutation sites by way of directed screening. The monooxygenase mutant has the advantage of greatly improved stereoselectivity, and the enzyme activity is also improved correspondingly.

According to a typical embodiment of the present disclosure, a DNA molecule is provided. The DNA molecule encodes the monooxygenase mutant. The monooxygenase obtained by encoding the DNA improves the enzymatic activity and the stereoselectivity of the enzyme. The amount of the enzyme added into the monooxygenation reaction of catalyzing the thioether compound or the ketone compound can be reduced, such that the post-treatment difficulty is reduced.

The above DNA molecule of the disclosure may also exist in the form of an "expression cassette". The "expression cassette" refers to a linear or circular nucleic acid molecule that encompasses DNA and RNA sequences capable of guiding expression of a specific nucleotide sequence in an appropriate host cell. Generally, including a promoter which is effectively linked with a target nucleotide, it is optionally effectively linked with a termination signal and/or other control elements. The expression cassette may also include a sequence required for proper translation of the nucleotide sequence. A coding region usually encodes a target protein, but also encodes a target function RNA in a sense or antisense direction, for example an antisense RNA or an untranslated RNA. The expression cassette including a target polynucleotide sequence may be chimeric, which means that at least one of components thereof is heterologous to at least one of the other components thereof. The expression cassette may also be existent naturally, but obtained with effective recombinant formation for heterologous expression.

According to a typical embodiment of the present disclosure, a recombinant plasmid is provided. The recombinant plasmid contains the above any one DNA molecule. The DNA molecule in the recombinant plasmid is placed in a proper position of the recombinant plasmid, such that the DNA molecule can be duplicated, transcribed or expressed correctly and smoothly.

Although a qualifier used in the disclosure while the above DNA molecule is defined is "contain", it does not mean that other sequences which are not related to a function thereof may be arbitrarily added to both ends of the DNA sequence. Those skilled in the art know that in order to meet the requirements of recombination operations, it is necessary to add suitable enzyme digestion sites of a restriction enzyme at two ends of the DNA sequence, or additionally increase a start codon, a termination codon and the like, therefore, if the closed expression is used for defining, these situations may not be covered truly.

The term "plasmid" used in the disclosure includes any plasmids, cosmids, bacteriophages or *agrobacterium* binary nucleic acid molecules in double-strand or single-strand linear or circular form, preferably a recombinant expression plasmid, which may be a prokaryotic expression plasmid or may be a eukaryotic expression plasmid, preferably the prokaryotic expression plasmid, in some implementation, the recombinant expression plasmid is selected from pET-22b(+), pET-22b(+), pET-3a(+), pET-3d(+), pET-11a(+), pET-12a(+), pET-14b(+), pET-15b(+), pET-16b(+), pET-17b (+), pET-19b(+), pET-20b(+), pET-21a(+), pET-23a(+), pET-23b(+), pET-24a(+), pET-25b(+), pET-26b(+), pET-27b (+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b (+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the recombinant plasmid is pET-22b (+).

According to a typical embodiment of the present disclosure, a host cell is provided. The host cell includes the above any one recombinant plasmid. The host cell suitable for the present disclosure includes, but not limited to, prokaryotic cell, yeast or eukaryocyte. Preferably, the prokaryotic cell is a *Eubacterium*, for example, a gram-negative bacterium or a gram-positive bacterium. More preferably, the prokaryotic cell is an *Escherichia coli* BL21 cell or an *Escherichia coli* DH5a competent cell. The optimum condition for inducible expression of monooxygenase is as follows: the monooxygenase is induced by 0.2 mM IPTG for 16 h at 25° C. The mutant plasmid is transformed into the *Escherichia coli* cell and then a crude enzyme is obtained by a method of ultrasonication of cells.

According to a typical embodiment of the present disclosure, use of the monooxygenase mutant in a monooxygenation reaction of catalyzing a thioether compound or a ketone compound is provided. The monooxygenase is the above any one monooxygenase mutant. As the monooxygenase mutant of the present disclosure is higher in enzyme catalytic activity, the production cost can be lowered and a more chirally pure product is obtained in industrial production of the monooxygenase mutant.

In a typical embodiment, the thioether compound is

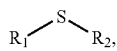

wherein $R_1$ and $R_2$ independently represent optionally substituted or unsubstituted alkyl, optionally substituted or unsubstituted aralkyl or optionally substituted or unsubstituted aryl respectively. In addition, $R_1$ and $R_2$ can independently form optionally substituted or unsubstituted rings or can form optionally substituted or unsubstituted rings in a combined manner. $R_1$ and $R_2$ are optionally substituted or unsubstituted alkyl, optionally substituted or unsubstituted aralkyl, or optionally substituted or unsubstituted aryl with 1-20 carbon atoms, more preferably optionally substituted or unsubstituted alkyl, optionally substituted or unsubstituted aralkyl, or optionally substituted or unsubstituted aryl with 1-10 carbon atoms. As the aryl, phenyl, naphthyl, pyridyl, thienyl, oxadiazolyl, imidazolyl, thiazolyl, furyl, pyrryl, phenoxyl, naphthoxyl, pyridinyloxy, thienyloxy, oxadiazolyloxy, imidazolyloxy, thiazolyloxy, furyloxy, pyrrolyloxy and the like can be listed. As the alkyl, methyl, ethyl, propyl, butyl, pentyl, hexyl, isopropyl, sec-butyl, tertiary butyl, methoxyl, ethoxyl, tert-butoxyl, methoxycarbonyl, ethoxycarbonyl, tert-butoxycarbonyl, vinyl, allyl, cyclopentyl, cycloheptyl and the like can be listed. As the aralkyl, benzyl and the like can be listed. These radicals further can be substituted. As its substituents, a halogen atom, a nitrogen atom, a sulfur atom, hydroxyl, nitryl, cyano, methoxyl, ethoxyl, carboxyl, carboxymethyl, carboxymethyl or methylenedioxyl and the like can be listed. In addition, the ring can be further formed by these substituents. The ketone compound is

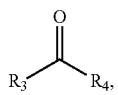

wherein $R_3$ and $R_4$ independently represent optionally substituted or unsubstituted alkyl, optionally substituted or unsubstituted aralkyl or optionally substituted or unsubstituted aryl respectively. In addition, $R_3$ and $R_4$ can independently form optionally substituted or unsubstituted rings or can form optionally substituted or unsubstituted rings in a combined manner. $R_3$ and $R_4$ are optionally substituted or unsubstituted alkyl, optionally substituted or unsubstituted aralkyl, or optionally substituted or unsubstituted aryl with 1-20 carbon atoms, more preferably optionally substituted or unsubstituted alkyl, optionally substituted or unsubstituted aralkyl, or optionally substituted or unsubstituted aryl with 1-10 carbon atoms; as the aryl, phenyl, naphthyl, pyridyl, thienyl, oxadiazolyl, imidazolyl, thiazolyl, furyl, pyrryl, phenoxyl, naphthoxyl, pyridinyloxy, thienyloxy, oxadiazolyloxy, imidazolyloxy, thiazolyloxy, furyloxy, pyrrolyloxy and the like can be listed. As the alkyl, methyl, ethyl, propyl, butyl, pentyl, hexyl, isopropyl, sec-butyl, tertiary butyl, methoxyl, ethoxyl, tert-butoxyl, methoxycarbonyl, ethoxycarbonyl, tert-butoxycarbonyl, vinyl, allyl, cyclopentyl, cycloheptyl and the like can be listed. As the aralkyl, benzyl and the like can be listed. These radicals further can be substituted. As its substituents, a halogen atom, a nitrogen atom, a sulfur atom, hydroxyl, nitryl, cyano, methoxyl, ethoxyl, carboxyl, carboxymethyl, carboxymethyl or methylenedioxyl and the like can be listed. In addition, the ring can be further formed by these substituents.

A reaction equation is as follows:

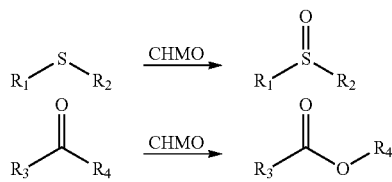

According to a typical embodiment of the present disclosure, the monooxygenase mutant of the present disclosure is applied to synthesis of a side chain of sulopenem. The reaction equation is as follows:

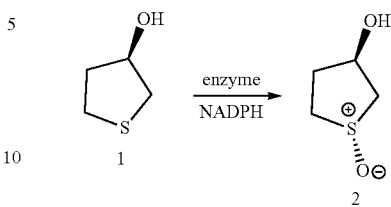

The monooxygenase mutant obtained by the present disclosure can be used for synthesizing the side chain of sulopenem, an exothermic reaction is avoided and (R,R)-1-oxo-3-hydroxyl tetrahydrothiophene with high optical purity (the conversation ratio is greater than 99% and the ee value is 95.0%) is obtained. The industrial production cost of the compound is lowered greatly, such that the enzyme is better in application value in industrial production.

The monooxygenase can be a solution, lyophilized powder, an immobilized enzyme or an immobilized cell of the monooxygenase mutant.

Preferably, a cofactor of catalyzing the monooxygenation reaction is NAD+/NADH and/or NADP+/NADPH. A circulatory system of the cofactor includes glucose and glucose dehydrogenase, formate and formate dehydrogenase, glucose-6-phosphoric acid and glucose-6-phosphate dehydrogenase or secondary alcohol (for example, isopropanol) or secondary alcohol dehydrogenase and similar systems, most preferably, isopropanol and alcohol dehydrogenase.

Preferably, the temperature of the catalytic monooxygenation reaction is 10-37° C., more preferably 15-35° C.; the time of the catalytic monooxygenation reaction is 3-48 h, more preferably 6-16 h; the catalytic monooxygenation reaction is conducted under a condition that the pH is 6.0-10.0, more preferably 6.0-9.0; under the reaction condition, catalytic performance of the enzyme can be exerted better.

Detail description on beneficial effects of the present disclosure will be made below in combination with the embodiments.

Example 1

Reaction Characteristic Comparison in Preparation of (R,R)-1-oxo-3-hydroxyl tetrahydrothiophene by Site-Directed Mutation of Monooxygenase In a 50 mL glass triangular flask, 100 mg of (R)-3-hydroxyltetrahydrothiophene is added into 850 μL of isopropanol and the two are mixed uniformly, the pH is adjusted to 6.0-9.0, then the mixture is added into a crude enzyme containing 800 mg of monooxygenase, 0.12 g of isopropanol dehydrogenase, 50 μL (20 mg/mL) NADP+ and 0.1 M of Tris-HCl buffer, the total reaction volume is 10 mL, the pH of the system is 6.0-9.0, and a flask shaking reaction at a constant temperature is conducted at 15-30° C. In 16 h, 700 μL of a reaction system is taken, 1.4 mL of absolute ethyl alcohol is added, centrifugalization is conducted for 5 min at 12000 rpm, 0.5 g of anhydrous $MgSO_4$ into a supernatant to dehydrate, centrifugalization is conducted for 5 min at 12000 rpm, the supernatant is taken and is dried with $N_2$ and is re-dissolved with 700 μL of absolute ethyl alcohol and the mixture is analyzed by GC. Part of reaction characteristics of the mutants are as shown in a table 1:

TABLE 1

| Mutant | Conversion ratio | e.e. |
| --- | --- | --- |
| Wild | + | * |
| F508M | ++ | * |
| F508Y | +++ | ** |
| F508N | + | ** |
| F435S | +++ | ** |
| F435N | +++ | * |
| F435A | +++ | * |
| F435Y | +++ | * |
| L147Y | ++ | ** |
| L147T | + | ** |
| L147M | ++ | ** |
| L146F | + | ** |
| L146Y | + | ** |
| F280Y | ++ | * |
| L429Y | ++ | * |
| T436A | +++ | ** |
| T436S | ++ | ** |
| L438A | ++ | ** |
| L438F | ++ | ** |
| L438S | ++ | ** |
| I494A | ++ | ** |
| W493A | ++ | * |
| L510V | ++ | * |

Those with the conversion ratios of 10-50% are as shown by +, those with the conversion ratios of 50-90% are as shown by ++ and those with the conversion ratios of over 90% are as shown by +++; those with the ee values of −99%−−50% are as shown by * and those with the ee values of −50%-0% are as shown by **.

Compared with a female parent, the stereoselectivity and activity of the single-site mutant are improved but do not reach the most ideal effect. Therefore, a more excellent mutant can be obtained by combining different beneficial active sites.

Example 2

Reaction Characteristic Comparison in Preparation of (R, R)-1-oxo-3-hydroxyl tetrahydrothiophene by Combined Mutation of Monooxygenase In a 50 mL glass triangular flask, 100 mg of (R)-3-hydroxyltetrahydrothiophene is added into 850 μL of isopropanol and the two are mixed uniformly, the pH is adjusted to 6.0-9.0, then the mixture is added into a crude enzyme containing 800 mg of monooxygenase, 0.12 g of isopropanol dehydrogenase, 50 μL (20 mg/mL) NADP+ and 0.1 M of Tris-HCl buffer, the total reaction volume is 10 mL, the pH of the system is 6.0-9.0, and a flask shaking reaction at a constant temperature is conducted at 15-30° C. In 16h, 700 μL of a reaction system is taken, 1.4 mL of absolute ethyl alcohol is added, centrifugalization is conducted for 5 min at 12000 rpm, 0.5 g of anhydrous MgSO₄ into a supernatant to dehydrate, centrifugalization is conducted for 5 min at 12000 rpm, the supernatant is taken and is dried with N2 and is re-dissolved with 700 μL of absolute ethyl alcohol and the mixture is analyzed by GC. Part of reaction characteristics of the mutant is as shown in a table 2:

TABLE 2

| Mutant | Conversion ratio | e.e. |
| --- | --- | --- |
| Wild | + | * |
| F435A + F508Y | +++ | *** |
| F435S + F508Y | ++ | ** |
| L147Y + F508M | ++ | *** |
| F280Y + F508M | ++ | ** |
| F280Y + F508N | +++ | ** |
| F435A + L510V | +++ | *** |
| F435S + L510V | ++ | ** |
| F435N + L510V | +++ | *** |
| T436A + L510V | +++ | *** |
| L438A + L510V | +++ | ** |
| T436A + L438A | +++ | ** |
| F435A + T436A | +++ | ** |
| F435S + T436A | +++ | *** |
| F435N + T436A | +++ | ** |
| L146Y + F508M | ++ | *** |
| L146F + F508M | ++ | ** |
| F280Y + F508Y | +++ | ** |
| F280Y + F508N | ++ | ** |
| F435A + T436A + F508Y | ++ | ** |
| F435A + T436A + F508M | ++ | ** |
| F435A + T436A + L510V | +++ | ** |
| F435S + T436A + L510V | ++ | *** |
| T436A + L438A + F508Y | ++ | ** |
| T436A + L438A + F508M | ++ | ** |
| T436A + L438A + F508N | +++ | *** |
| L147Y + F435A + F508M | ++ | *** |
| L147Y + F435A + F508Y | ++ | ** |
| L147Y + F435A + F508N | ++ | * |
| L147Y + F435S + F508Y | +++ | ** |
| L147Y + F435N + F508Y | ++ | ** |
| L147Y + F435S + F508Y | +++ | *** |
| L147Y + F435N + F508Y | +++ | ** |

Those with the conversion ratios of 10-50% are as shown by +, those with the conversion ratios of 50-90% are as shown by ++ and those with the conversion ratios of over 90% are as shown by +++; those with the ee values of −99%−−50% are as shown by *, those with the ee values of −50%-0% are as shown by , those with the ee values of 0%-20% are as shown by *, those with the ee values of 20%-60% are as shown by **, those with the ee values of 60%-80% are as shown by *** and those with the ee values of 80%-99% are as shown by *.

Example 3

Reaction Characteristic Comparison in Preparation of (R, R)-1-oxo-3-hydroxyl Tetrahydrothiophene by Saturated Mutation of Monooxygenase In a 50 mL glass triangular flask, 100 mg of (R)-3-hydroxyltetrahydrothiophene is added into 850 μL of isopropanol and the two are mixed uniformly, the pH is adjusted to 6.0-9.0, then the mixture is added into a crude enzyme containing 800 mg of monooxygenase, 0.12 g of isopropanol dehydrogenase, 50 μL (20 mg/mL) NADP+ and 0.1 M of Tris-HCl buffer, the total reaction volume is 10 mL, the pH of the system is 6.0-9.0, and a flask shaking reaction at a constant temperature is conducted at 15-30° C. In 16 h, 700 μL of a reaction system is taken, 1.4 mL of absolute ethyl alcohol is added, centrifugalization is conducted for 5 min at 12000 rpm, 0.5 g of anhydrous MgSO₄ into a supernatant to dehydrate, centrifugalization is conducted for 5 min at 12000 rpm, the supernatant is taken and is dried with N₂ and is re-dissolved with 700 μL of absolute ethyl alcohol and the mixture is analyzed by GC. Part of reaction characteristics of the mutant is as shown in a table 3:

TABLE 3

| Mutant | Activity | e.e. |
|---|---|---|
| Wild | + | * |
| F508Y + F435A + L438A | +++ | **** |
| F508Y + F435A + L438Y | +++ | **** |
| F508Y + F435A + L438Y | +++ | *** |
| F508Y + F435A + L438A + T436A | +++ | ***** |
| F508Y + F435A + L438A + T436S | +++ | ***** |
| F508M + F435A + L438A + T436A | +++ | **** |
| F508M + F435A + L438A + T436S | +++ | ***** |
| F508Y + F435A + L438A + T436A + F280W | +++ | ****** |
| F508Y + F435A + L438A + T436A + F280A | +++ | ****** |
| F508Y + F435A + L438A + T436A + S441L | +++ | ****** |
| F508M + F435A + L438A + T436A + F280W | +++ | ****** |
| F508M + F435A + L438A + T436A + F280V | +++ | ****** |
| F508M + F435A + L438A + T436A + S441V | +++ | ****** |
| F508M + F435A + L438A + T436A + S441A | +++ | **** |
| F508Y + F435N + L438A + T436S | +++ | ****** |
| F508Y + F435N + L438A + T436S + F280V | +++ | ****** |
| F508Y + F435N + L438A + T436S + S441L | +++ | ****** |
| F508Y + F435A + L438A + T436S + F280V + S441V | +++ | ****** |
| F508Y + F435N + L438A + T436S + F280V + S441V + L510V | +++ | ****** |
| F508M + F435N + L438A + T436S + F280V + S441V + L510V | +++ | ****** |
| F508M + F435A + L438A + T436S + F280V + S441V + L510V | +++ | ***** |
| F508M + F435S + L438A + T436S + F280V + S441V + L510V | +++ | ***** |
| F508Y + F435S + L438Y + T436S + F280V + S441V + L510V | +++ | ****** |
| F508Y + F435N + L438A + T436A + F280V + S441V + L510V | +++ | ****** |
| F508Y + F435N + L438A + T436A + F280V + S441A + L510V | +++ | ****** |
| F508Y + F435N + L438A + T436A + F280V + S441L + L510V | +++ | ****** |
| F508Y + F435N + L438A + T436A + F280V + S441L + L510V + L429Y + W493A + L146F + L147M + I494A | ++ | **** |
| F508Y + F435N + L438A + T436A + F280V + S441L + L510V + L429Y + W493A + L146F + L147Y + I494S | ++ | ****** |
| F508Y + F435N + L438A + T436A + F280V + S441L + L510V + L429Y + W493A + L146F + L147T + I494M | +++ | **** |
| F508Y + F435N + L438A + T436S + F280V + S441V + L510V + D60L | +++ | ****** |
| F508M + F435N + L438A + T436S + F280V + S441V + L510V + D60L + T61Q | +++ | ****** |
| F508Y + F435A + L438A + T436S + F280V + S441V + L510V + D60L + G145F | +++ | ***** |
| F508M + F435S + L438A + T436S + F280V + S441V + L510V + D60L + A169K | +++ | ***** |
| F508Y + F435S + L438Y + T436S + F280V + S441V + L510V + D60L + S189M | +++ | ****** |
| F508Y + F435N + L438A + T436A + F280V + S441V + L510V + D60L + L332R | +++ | ****** |
| F508Y + F435N + L438A + T436A + F280V + S441A + L510V + D60L + A328N | +++ | ****** |
| F508Y + F435N + L438A + T436A + F280V + S441L + L510V + D60L + G430A | +++ | ****** |
| F508Y + F435N + L438A + T436A + F280V + S441L + L510V + L429Y + W493A + L146F + L147M + I494A + D60L + N432Y | ++ | **** |
| F508Y + F435N + L438A + T436A + F280V + S441L + L510V + L429Y + W493A + L146F + L147Y + I494S + D60L + Y509M | ++ | ****** |
| F508Y + F435N + L438A + T436A + F280V + S441L + L510V + L429Y + W493A + L146F + L147T + I494M + D60L + G512I | +++ | **** |

The activities with the conversion ratios of 10-50% is as shown by +, those with the conversion ratios of 50-90% are as shown by ++ and those with the conversion ratios of over 90% are as shown by +++; those with the ee values of −99%--50% are as shown by *, those with the ee values of −50%-0% are as shown by , those with the ee values of 0%-20% are as shown by *, those with the ee values of 20%-60% are as shown by **, those with the ee values of 60%-80% are as shown by * and those with the ee values of 80%-99% are as shown by ****.

Via iterative saturated mutation, the mutation sites with improved stereoselectivity are overlapped to obtain the mutant with stably improved ee value. Meanwhile, combined saturated mutation is conducted on the amino acids at the active sites obtained by preliminary screening, so that in an evolutionary process, an evolution result is only limited to the local highest point rather than the global highest point. The mutant with the optimum stereoselectivity and activity is obtained finally.

Example 4

Reaction Characteristic Comparison in Preparation of (R, R)-1-oxo-3-hydroxyl Tetrahydrothiophene by Partial Mutant In a 50 mL glass triangular flask, 100 mg of (R)-3-hydroxyltetrahydrothiophene is added into 850 μL of isopropanol and the two are mixed uniformly, the pH is adjusted to 6.0-9.0, then the mixture is added into a crude enzyme containing 800 mg of monooxygenase, 0.12 g of isopropanol dehydrogenase, 50 μL (20 mg/mL) NADP+ and 0.1 M of Tris-HCl buffer, the total reaction volume is 10 mL, the pH of the system is 6.0-9.0, and a flask shaking reaction at a constant temperature is conducted at 15-30° C. In 16h, 700 μL of a reaction system is taken, 1.4 mL of absolute ethyl alcohol is added, centrifugalization is conducted for 5 min at 12000 rpm, 0.5 g of anhydrous MgSO₄ into a supernatant to dehydrate, centrifugalization is conducted for 5 min at 12000 rpm, the supernatant is taken and is dried with N2 and is re-dissolved with 700 μL of absolute ethyl alcohol and the mixture is analyzed by GC. Part of reaction characteristics of the mutant is as shown in a table 4:

TABLE 4

| Mutant | Activity | e.e. |
| --- | --- | --- |
| Wild | + | * |
| F508Y + F435A + L438A + W49A + D60L | +++ | **** |
| F508Y + F435A + L438A + V144E | +++ | **** |
| F508Y + F435A + L438A + G145F | +++ | **** |
| F508Y + F435A + L438A + T436A + H167W | +++ | **** |
| F508Y + F435A + L438A + T436A + A169K | +++ | **** |
| F508Y + F435A + L438A + T436A + S179M | +++ | **** |
| F508Y + F435A + L438A + T436A + A246V | +++ | **** |
| F508Y + F435A + L438A + T436A + V247T | +++ | **** |
| F508Y + F435A + L438A + T436A + F284S | +++ | **** |
| F508Y + F435A + L438A + T436A + G285A | +++ | **** |
| F508M + F435A + L438A + T436A + T286A | +++ | **** |
| F508M + F435A + L438A + T436A + R330A | +++ | **** |
| F508M + F435A + L438A + T436A + L332R | +++ | **** |
| F508M + F435A + L438A + T436A + A328N | +++ | **** |
| F508Y + F435A + L438A + T436S + G382A | +++ | **** |
| F508Y + F435A + L438A + T436S + M427I | +++ | **** |
| F508Y + F435A + L438A + T436S + V428A | +++ | **** |
| F508Y + F435A + L438A + T436S + G430A | +++ | **** |
| F508Y + F435A + L438A + T436S + P431A | +++ | **** |
| F508Y + F435A + L438A + T436S + N432Y | +++ | **** |
| F508Y + F435A + L438A + T436S + G433Y | +++ | **** |
| F508Y + F435A + L438A + T436S + P434A | +++ | ***** |
| F508Y + F435A + L438A + T436S + Y509M | +++ | ***** |

TABLE 4-continued

| Mutant | Activity | e.e. |
| --- | --- | --- |
| F508Y + F435A + L438A + T436S + G511L | +++ | ***** |
| F508Y + F435A + L438A + T436S + G512I | +++ | ***** |
| F508Y + F435A + L438A + T436S + L513V | +++ | ***** |

The activities with the conversion ratios of 10-50% is as shown by +, those with the conversion ratios of 50-90% are as shown by ++ and those with the conversion ratios of over 90% are as shown by +++; those with the ee values of −99%--−50% are as shown by *, those with the ee values of −50%-0% are as shown by , those with the ee values of 0%-20% are as shown by *, those with the ee values of 20%-60% are as shown by **, those with the ee values of 60%-80% are as shown by * and those with the ee values of 80%-99% are as shown by ****.

Example 5

Reaction Characteristic Comparison in Preparation of (R,R)-1-oxo-3-hydroxyl Tetrahydrothiophene by Monooxygenase In a 500 mL glass triangular flask, 1 g of (R)-3-hydroxyltetrahydrothiophene is added into 8.5 mL of isopropanol and the two are mixed uniformly, the pH is adjusted to 6.0-9.0, then the mixture is added into a crude enzyme containing 2 g of monooxygenase, 0.4 g of isopropanol dehydrogenase, 500 μL (20 mg/mL) NADP+ and 0.1 M of Tris-HCl buffer, the total reaction volume is 100 mL, the pH of the system is 6.0-9.0, and a flask shaking reaction at a constant temperature is conducted at 15-30° C. In 16 h, 700 μL of a reaction system is taken, 1.4 mL of absolute ethyl alcohol is added, centrifugalization is conducted for 5 min at 12000 rpm, 0.5 g of anhydrous MgSO₄ into a supernatant to dehydrate, centrifugalization is conducted for 5 min at 12000 rpm, the supernatant is taken and is dried with N2 and is re-dissolved with 700 μL of absolute ethyl alcohol and the mixture is analyzed by GC, wherein a reaction result is shown in a table 5:

TABLE 5

| Mutant | Activity | e.e. | Yield |
| --- | --- | --- | --- |
| Wild | + | * | # |
| F508Y + F435N + L438A + T436S + F280V + S441V | +++ | ****** | ### |
| F508Y + F435S + L438Y + T436S + F280V + S441V + L510V | +++ | ****** | ### |
| F508Y + F435N + L438A + T436A + F280V + S441V + L510V | +++ | ****** | ### |
| F508Y + F435N + L438A + T436A + F280V + S441A + L510V | +++ | ****** | ### |
| F508Y + F435N + L438A + T436A + F280V + S441L + L510V | +++ | ****** | ### |
| F508Y + F435N + L438A + T436A + F280V + S441L + L510V + L429Y + W493A + L146F + L147Y + I494S | ++ | ****** | ### |
| F508Y + F435N + L438A + T436A + F280V + S441L + L510V + L429Y + W493A + L146F + L147T + I494M | +++ | **** | ### |
| F508Y + F435S + L438Y + T436S + F280V + S441V + L510V + D60L | +++ | ****** | ### |
| F508Y + F435N + L438A + T436A + F280V + S441V + L510V + D60L + P431A | +++ | ****** | ### |
| F508Y + F435N + L438A + T436A + F280V + S441A + L510V + D60L | +++ | ****** | ### |
| F508Y + F435N + L438A + T436A + F280V + S441L + L510V + D60L | +++ | ****** | ### |
| F508Y + F435N + L438A + T436A + F280V + S441L + L510V + D60L + L429Y + W493A + L146F + L147Y + I494S | +++ | ****** | ### |
| F508Y + F435N + L438A + T436A + F280V + S441L + L510V + D60L + L429Y + W493A + L146F + L147T + I494M | +++ | ****** | ### |

The activities with the conversion ratios of 10-50% is as shown by +, those with the conversion ratios of 50-90% are as shown by ++ and those with the conversion ratios of over 90% are as shown by +++; those with the ee values of −99%--50% are as shown by *, those with the ee values of −50%-0% are as shown by , those with the ee values of 0%-20% are as shown by *, those with the ee values of 20%-60% are as shown by **, those with the ee values of 60%-80% are as shown by * and those with the ee values of 80%-99% are as shown by ****; and those with the yields of 0-20% are #, those with the yields of 20-40% are ##, and those with the yields of 40-60% are ###.

Example 6

Reaction Characteristic Comparison on a Substrate 4-methyl Cyclohexanone by the Monooxygenase Mutant In a 50 mL glass triangular flask, 100 mg of 4-methyl cyclohexanone is added into 850 μL of isopropanol and the two are mixed uniformly, the pH is adjusted to 6.0-9.0, then the mixture is added into a crude enzyme containing 800 mg of monooxygenase, 0.12 g of isopropanol dehydrogenase, 50 μL (20 mg/mL) NADP+ and 0.1 M of Tris-HCl buffer, the total reaction volume is 10 mL, the pH of the system is 6.0-9.0, and a flask shaking reaction at a constant temperature is conducted at 15-30° C. In 16h, 700 μL of a reaction system is taken, 1.4 mL of acetonitrile is added, centrifugalization is conducted for 5 min at 12000 rpm, and a supernatant is fed to HPLC for analysis. Reaction characteristics of the mutant are as shown in a table 6:

TABLE 6

| Mutant | Activity |
| --- | --- |
| Wild | + |
| F508Y + F435A + L438Y | ++ |
| F508Y + F435A + L438A + T436A | ++ |
| F508Y + F435A + L438A + T436S | ++ |
| F508M + F435A + L438A + T436A | ++ |
| F508M + F435A + L438A + T436S | ++ |
| F508Y + F435N + L438A + T436S + F280V + S441V | ++ |
| F508Y + F435N + L438A + T436S + F280V + S441V + L510V | ++ |
| F508M + F435N + L438A + T436S + F280V + S441V + L510V | +++ |
| F508M + F435A + L438A + T436S + F280V + S441V + L510V | ++ |
| F508M + F435S + L438A + T436S + F280V + S441V + L510V | +++ |
| F508Y + F435S + L438Y + T436S + F280V + S441V + L510V | +++ |
| F508Y + F435N + L438A + T436A + F280V + S441V + L510V | +++ |
| F508Y + F435N + L438A + T436A + F280V + S441A + L510V | +++ |
| F508Y + F435N + L438A + T436A + F280V + S441L + L510V | +++ |
| F508M + F435A + L438A + T436S + F280V + S441V + L510V + D60L + G145F | ++ |
| F508M + F435S + L438A + T436S + F280V + S441V + L510V + D60L + A169K | +++ |
| F508Y + F435S + L438Y + T436S + F280V + S441V + L510V + D60L + S189M | +++ |
| F508Y + F435N + L438A + T436A + F280V + S441V + L510V + D60L + L332R | +++ |
| F508Y + F435N + L438A + T436A + F280V + S441A + L510V + D60L + A328N | +++ |
| F508Y + F435N + L438A + T436A + F280V + S441L + L510V + D60L + G430A | +++ |
| F508Y + F435N + L438A + T436A + F280V + S441L + L510V + L429Y + W493A + L146F + L147M + I494A + D60L + N432Y | +++ |
| F508Y + F435N + L438A + T436A + F280V + S441L + L510V + L429Y + W493A + L146F + L147Y + I494S + D60L + Y509M | +++ |
| F508Y + F435N + L438A + T436A + F280V + S441L + L510V + L429Y + W493A + L146F + L147T + I494M + D60L + G512I | +++ |

The activities with the conversion ratios of 10-50% are as shown by +, those with the conversion ratios of 50-80% are as shown by ++ and those with the conversion ratios of over 80% are as shown by +++.

Example 7

Reaction Characteristic Comparison on a Substrate Thioanisole by the Monooxygenase Mutant In a 50 mL glass triangular flask, 100 mg of thioanisole is added into 850 μL of isopropanol and the two are mixed uniformly, the pH is adjusted to 6.0-9.0, then the mixture is added into a crude enzyme containing 800 mg of monooxygenase, 0.12 g of isopropanol dehydrogenase, 50 μL (20 mg/mL) NADP+ and 0.1 M of Tris-HCl buffer, the total reaction volume is 10 mL, the pH of the system is 6.0-9.0, and a flask shaking reaction at a constant temperature is conducted at 15-30° C. In 16h, 700 μL of a reaction system is taken, 1.4 mL of acetonitrile is added, centrifugalization is conducted for 5 min at 12000 rpm, and a supernatant is fed to HPLC for analysis. Part of reaction characteristics of the mutant is as shown in a table 7:

TABLE 7

| Mutant | Activity | e.e. |
|---|---|---|
| Wild | + | * |
| F508Y + F435A + L438A | ++ | ** |
| F508Y + F435A + L438Y | ++ | *** |
| F508Y + F435A + L438Y | ++ | *** |
| F508Y + F435A + L438A + T436A | ++ | *** |
| F508Y + F435A + L438A + T436S | ++ | *** |
| F508M + F435A + L438A + T436A | ++ | *** |
| F508M + F435A + L438A + T436S | +++ | *** |
| F508Y + F435A + L438A + T436A + F280W + D60L | +++ | *** |
| F508Y + F435A + L438A + T436A + F280A + V247T | +++ | **** |
| F508Y + F435A + L438A + T436A + S441L + F285A | +++ | **** |
| F508Y + F435N + L438A + T436S + R330A | +++ | **** |
| F508Y + F435N + L438A + T436S + F280V + G430A | +++ | **** |
| F508Y + F435N + L438A + T436S + S441L + P434A | +++ | **** |
| F508Y + F435N + L438A + T436S + F280V + S441V | +++ | **** |
| F508Y + F435N + L438A + T436S + F280V + S441V + L510V | +++ | **** |
| F508M + F435N + L438A + T436S + F280V + S441V + L510V | +++ | **** |
| F508M + F435A + L438A + T436S + F280V + S441V + L510V | +++ | **** |
| F508M + F435S + L438A + T436S + F280V + S441V + L510V | +++ | **** |
| F508Y + F435S + L438Y + T436S + F280V + S441V + L510V | +++ | **** |
| F508Y + F435N + L438A + T436A + F280V + S441V + L510V | +++ | **** |
| F508Y + F435N + L438A + T436A + F280V + S441A + L510V | +++ | **** |
| F508Y + F435N + L438A + T436A + F280V + S441V + L510V | +++ | **** |
| F508M + F435N + L438A + T436S + F280V + S441V + L510V + Q60L + T286A + Y509M | +++ | **** |
| F508M + F435A + L438A + T436S + F280V + S441V + L510V + Q60L + T61Q + V247T | +++ | **** |
| F508M + F435S + L438A + T436S + F280V + S441V + L510V + Q60L + F287D + R330A | +++ | **** |
| F508Y + F435S + L438Y + T436S + F280V + S441V + L510V + V144E + G145F + M427I | +++ | **** |
| F508Y + F435N + L438A + T436A + F280V + S441V + L510V + Q60L + L322R + N432Y | +++ | **** |
| F508Y + F435N + L438A + T436A + F280V + S441A + L510V + R330A + P321A + G512I | +++ | **** |
| F508Y + F435N + L438A + T436A + F280V + S441L + L510V + T61Q + R330A + G430A | +++ | **** |

The activities with the conversion ratios of 10-50% is as shown by +, those with the conversion ratios of 50-90% are as shown by ++ and those with the conversion ratios of over 90% are as shown by +++; those with the ee values of 0%-20% are as shown by *, those with the ee values of 20%-60% are as shown by , those with the ee values of 60%-80% are as shown by * and those with the ee values of 80%-99% are as shown by ****.

The above is merely preferred embodiments of the present disclosure and is not used to limit the present disclosure. For those skilled in the art, various alternations and changes can be made on the present disclosure. Any modification, equivalent replacement, improvement, etc. made within the spirit and principle of the present disclosure shall be regarded as within the protection scope of the present disclosure.

What is claimed is:

1. A monooxygenase mutant having a monooxygenase activity, wherein the monooxygenase mutant comprises all of SEQ ID NO: 1 except for one of the following mutation site combinations:

F435A+F508Y; F435S+F508Y; L147Y+F508M; F280Y+F508M; F280Y+F508N;

L146Y+F508M; L146F+F508M; F280Y+F508Y; F280Y+F508N; F435A+T436A+F508Y;

F435A+T436A+F508M; T436A+L438A+F508Y; T436A+L438A+F508M;

T436A+L438A+F508N; L147Y+F435A+F508M; L147Y+F435A+F508Y;

L147Y+F435A+F508N; L147Y+F435S+F508Y; L147Y+F435N+F508Y;

L147Y+F435S+F508Y; L147Y+F435N+F508Y; F508Y+F435A+L438A;

F508Y+F435A+L438Y; F508Y+F435A+L438Y; F508Y+F435A+L438A+T436A;

F508Y+F435A+L438A+T436S; F508M+F435A+L438A+T436A;

F508M+F435A+L438A+T436S; F508Y+F435A+L438A+T436A+F280W;

F508Y+F435A+L438A+T436A+F280A; F508Y+F435A+L438A+T436A+S441L;

F508M+F435A+L438A+T436A+F280W; F508M+F435A+L438A+T436A+F280V;

F508M+F435A+L438A+T436A+S441V; F508M+F435A+L438A+T436A+S441A;

F508Y+F435N+L438A+T436S; F508Y+F435N+L438A+T436S+F280V;

F508Y+F435N+L438A+T436S+S441L; F508Y+F435N+L438A+T436S+F280V+S441V;

F508Y+F435N+L438A+T436S+F280V+S441V+L510V;

F508M+F435N+L438A+T436S+F280V+S441V+L510V;

F508M+F435A+L438A+T436S+F280V+S441V+L510V;

F508M+F435S+L438A+T436S+F280V+S441V+L510V;

F508Y+F435S+L438Y+T436S+F280V+S441V+L510V;

F508Y+F435N+L438A+T436A+F280V+S441V+L510V;

F508Y+F435N+L438A+T436A+F280V+S441A+L510V;

F508Y+F435N+L438A+T436A+F280V+S441L+L510V;

F508Y+F435N+L438A+T436A+F280V+S441L+L510V+L429Y+W493A+L146F+L147M+I494A;

F508Y+F435N+L438A+T436A+F280V+S441L+L510V+L429Y+W493A+L146F+L147Y+I494S;

F508Y+F435N+L438A+T436A+F280V+S441L+L510V+L429Y+W493A+L146F+L147T+I 494M;

F508Y+F435N+L438A+T436S+F280V+S441V+L510V+D60L;

F508M+F435N+L438A+T436S+F280V+S441V+L510V+D60L+T61Q;

F508M+F435A+L438A+T436S+F280V+S441V+L510V+D60L+G145F;

F508M+F435S+L438A+T436S+F280V+S441V+L510V+D60L+A169K;

F508Y+F435S+L438Y+T436S+F280V+S441V+L510V+D60L+S189M;

F508Y+F435N+L438A+T436A+F280V+S441V+L510V+D60L+L332R;

F508Y+F435N+L438A+T436A+F280V+S441A+L510V+D60L+A328N;

F508Y+F435N+L438A+T436A+F280V+S441L+L510V+D60L+G430A;

F508Y+F435N+L438A+T436A+F280V+S441L+L510V+L429Y+W493A+L146F +L147M +I494A+D60L+N432Y; F508Y+F435N+L438A+T436A+F280V+S441L+L510V +L429Y+W493A+L146F+L147Y+I494S+D60L+Y509M;

F508Y+F435N+L438A+T436A+F280V+S441L+L510V+L429Y+W493A+L146F+L147T+I 494M+D60L+G512I; F508Y+F435A+L438A+W49A+D60L;

F508Y+F435A+L438A+V144E; F508Y+F435A+L438A+G145F;

F508Y+F435A+L438A+T436A+H167W; F508Y+F435A+L438A+T436A+A169K;

F508Y+F435A+L438A+T436A+S179M; F508Y+F435A+L438A+T436A+A246V;

F508Y+F435A+L438A+T436A+V247T; F508Y+F435A+L438A+T436A+F284S;

F508Y+F435A+L438A+T436A+G285A; F508M+F435A+L438A+T436A+T286A;

F508M+F435A+L438A+T436A+R330A; F508M+F435A+L438A+T436A+L332R;

F508M+F435A+L438A+T436A+A328N; F508Y+F435A+L438A+T436S+G382A;

F508Y+F435A+L438A+T436S+M427I; F508Y+F435A+L438A+T436S+V428A;

F508Y+F435A+L438A+T436S+G430A; F508Y+F435A+L438A+T436S+P431A;

F508Y+F435A+L438A+T436S+N432Y; F508Y+F435A+L438A+T436S+G433Y;

F508Y+F435A+L438A+T436S+P434A; F508Y+F435A+L438A+T436S +Y509M;

F508Y+F435A+L438A+T436S+G511L; F508Y+F435A+L438A+T436S+G512I;

F508Y+F435A+L438A+T436S+L513V;

F508Y+F435S+L438Y+T436S+F280V+S441V+L510V+D60L;

F508Y+F435N+L438A+T436A+F280V+S441V+L510V+D60L+P431A;

F508Y+F435N+L438A+T436A+F280V+S441A+L510V+D60L;

F508Y+F435N+L438A+T436A+F280V+S441L+L510V+D60L;

F508Y+F435N+L438A+T436A+F280V+S441L+L510V+D60L+L429Y+W493A+L146F+L 147Y+I494S;

F508Y+F435N+L438A+T436A+F280V+S441L+L510V+D60L+L429Y+W493A+L146F+L147T+1494M; F508Y+F435A+L438Y; F508Y+F435A+L438A+T436A;
F508Y+F435A+L438A+T436S; F508M+F435A+L438A+T436A;
F508M+F435A+L438A+T436S; F508Y+F435A+L438A; F508Y+F435A+L438Y;
F508Y+F435A+L438Y; F508Y+F435A+L438A+T436A; F508Y+F435A+L438A+T436S;
F508M+F435A+L438A+T436A; F508M+F435A+L438A+T436S;
F508Y+F435A+L438A+T436A+F280W+D60L;
F508Y+F435A+L438A+T436A+F280A+V247T;
F508Y+F435A+L438A+T436A+S441L+F285A;
F508Y+F435N+L438A+T436S+R330A;
F508Y+F435N+L438A+T436S+F280V+G430A;
F508Y+F435N+L438A+T436S+S441L+P434A;
F508M+F435N+L438A+T436S+F280V+S441V+L510V+Q60L+T286A+Y509M;
F508M+F435A+L438A+T436S+F280V+S441V+L510V+Q60L+T61Q+V247T;
F508M+F435S+L438A+T436S+F280V+S441V+L510V+Q60L+F287D+R330A;
F508Y+F435S+L438Y+T436S+F280V+S441V+L510V+V144E+G145F+M427I;
F508Y+F435N+L438A+T436A+F280V+S441V+L510V+Q60L+L322R+N432Y;
F508Y+F435N+L438A+T436A+F280V+S441A+L510V+R330A+P321A+G512I; and
F508Y+F435N+L438A+T436A+F280V+S441L+L510V+T61Q+R330A+G430A.

2. A DNA molecule, wherein the DNA molecule encodes the monooxygenase mutant of claim 1.

3. A recombinant plasmid, wherein the recombinant plasmid comprises the DNA molecule of claim 2.

4. The recombinant plasmid of claim 3, wherein the recombinant plasmid is pET-22b(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

5. A host cell, wherein the host cell comprises the recombinant plasmid of claim 3.

6. The host cell of claim 5, wherein the host cell comprises prokaryotic cell or eukaryotic cell; preferably, the prokaryotic cell is escherichia coli BL21 cell or escherichia coli DH5α competent cell; and the eukaryotic cell is yeast.

7. A method for monooxygenation reaction comprising catalyzing a monooxygenation reaction of a thioether compound or a ketone compound by the monooxygenase mutant of claim 1.

8. The method of claim 7, wherein the thioether compound is

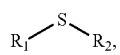

wherein $R_1$ and $R_2$ independently represent optionally substituted or unsubstituted alkyl, optionally substituted or unsubstituted aralkyl or optionally substituted or unsubstituted aryl respectively; and R1 and R2 can independently form optionally substituted or unsubstituted rings or can form optionally substituted or unsubstituted rings in a combined manner;
preferably, $R_1$ and $R_2$ are optionally substituted or unsubstituted alkyl, optionally substituted or unsubstituted aralkyl, or optionally substituted or unsubstituted aryl with 1-20 carbon atoms, more preferably optionally substituted or unsubstituted alkyl, optionally substituted or unsubstituted aralkyl, or optionally substituted or unsubstituted aryl with 1-10 carbon atoms;
preferably, the aryl comprises phenyl, naphthyl, pyridyl, thienyl, oxadiazolyl, imidazolyl, thiazolyl, furyl, pyrryl, phenoxyl, naphthoxyl, pyridyloxy, thienyloxy, oxadiazolyloxy, imidazolyloxy, thiazolyloxy, furyloxy and pyrrolyoxy;
preferably, the alkyl comprises methyl, ethyl, propyl, butyl, pentyl, hexyl, isopropyl, sec-butyl, tertiary butyl, methoxyl, ethoxyl, tert-butoxyl, methoxycarbonyl, ethoxycarbonyl, tert-butoxycarbonyl, vinyl, allyl, cyclopentyl and cycloheptyl;
preferably, the aralkyl is benzyl;
and preferably, being substituted means being substituted by halogen atom, nitrogen atom, sulfur atom, hydroxyl, nitryl, cyano, methoxyl, ethoxyl, carboxyl, carboxymethyl, carboxymethyl or methylenedioxyl.

9. The method of claim 7, wherein the ketone compound is

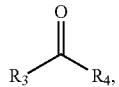

wherein $R_3$ and $R_4$ independently represent optionally substituted or unsubstituted alkyl, optionally substituted or unsubstituted aralkyl or optionally substituted or unsubstituted aryl respectively; and $R_3$ and $R_4$ can independently form optionally substituted or unsubstituted rings or can form optionally substituted or unsubstituted rings in a combined manner;
preferably, $R_3$ and $R_4$ are optionally substituted or unsubstituted alkyl, optionally substituted or unsubstituted aralkyl, or optionally substituted or unsubstituted aryl with 1-20 carbon atoms, more preferably optionally substituted or unsubstituted alkyl, optionally substituted or unsubstituted aralkyl, or optionally substituted or unsubstituted aryl with 1-10 carbon atoms;
preferably, the aryl comprises phenyl, naphthyl, pyridyl, thienyl, oxadiazolyl, imidazolyl, thiazolyl, furyl, pyrryl, phenoxyl, naphthoxyl, pyridyloxy, thienyloxy, oxadiazolyloxy, imidazolyloxy, thiazolyloxy, furyloxy and pyrrolyoxy;
preferably, the alkyl comprises methyl, ethyl, propyl, butyl, pentyl, hexyl, isopropyl, sec-butyl, tertiary butyl, methoxyl, ethoxyl, tert-butoxyl, methoxycarbonyl, ethoxycarbonyl, tert-butoxycarbonyl, vinyl, allyl, cyclopentyl and cycloheptyl;
preferably, the aralkyl is benzyl;
and preferably, being substituted means being substituted by halogen atom, nitrogen atom, sulfur atom, hydroxyl, nitryl, cyano, methoxyl, ethoxyl, carboxyl, carboxymethyl, carboxymethyl or methylenedioxyl.

10. The method of claim 7, wherein the use is synthesis of a side chain of sulopenem.

11. The method of claim 7, wherein the monooxygenase is a solution, lyophilized powder, an immobilized enzyme or an immobilized cell of the monooxygenase mutant of claim 1.

12. The method of claim 7, wherein a reaction system of the monooxygenation reaction comprises a cofactor, the cofactor is NAD+/NADH and/or NADP+/NADPH, and a circulatory system of the cofactor comprises glucose and glucose dehydrogenase, formate and formate dehydrogenase, glucose-6-phosphoric acid and glucose-6-phosphate dehydrogenase or secondary alcohol or secondary alcohol dehydrogenase.

13. The method of claim 7, wherein the temperature of the monooxygenation reaction is 10 to 37° C.

14. The method of claim 7, wherein the time of the monooxygenation reaction is 3 to 48 hours.

15. The method of claim 7, wherein the monooxygenation reaction is carried out at a pH of 5.0 to 10.0.

16. The method of claim 7, wherein the temperature of the monooxygenation reaction is 15 to 35° C.

17. The method of claim 7, wherein the time of the monooxygenation reaction is 6 to 16 hours.

18. The method of claim 7, wherein the monooxygenation reaction is carried out at a pH of 6.0 to 9.0.

* * * * *